United States Patent [19]

Sergio et al.

[11] 4,397,617
[45] Aug. 9, 1983

[54] HEART PUMP FOR THE CIRCULATION OF BLOOD OUTSIDE THE BODY OF A LIVING SUBJECT

[75] Inventors: Carbonini Sergio; Giancarlo Pelosi, both of Rome, Italy

[73] Assignee: Consiglio Nazionale Delle Ricerche, Rome, Italy

[21] Appl. No.: 199,494

[22] Filed: Oct. 22, 1980

[30] Foreign Application Priority Data

May 12, 1980 [IT] Italy ................................ 21982 A/80

[51] Int. Cl.³ ............................................. F04B 43/12
[52] U.S. Cl. ..................................... 417/475; 417/479
[58] Field of Search ............... 417/394, 474, 475, 478, 417/479, 480

[56] References Cited

U.S. PATENT DOCUMENTS

| | | | |
|---|---|---|---|
| 2,291,912 | 8/1942 | Meyer | 417/474 X |
| 3,007,416 | 11/1961 | Childs | 417/479 X |
| 3,039,309 | 6/1962 | Vesper et al. | 417/394 X |
| 3,154,021 | 10/1964 | Vick, Jr. | 417/394 |
| 3,175,498 | 3/1965 | Rohrer | 417/474 |

FOREIGN PATENT DOCUMENTS

| | | | |
|---|---|---|---|
| 894503 | 9/1953 | Fed. Rep. of Germany | 417/474 |
| 2230764 | 1/1974 | Fed. Rep. of Germany | 417/479 |

*Primary Examiner*—Leonard E. Smith
*Attorney, Agent, or Firm*—Bucknam and Archer

[57] ABSTRACT

A heart pump for the circulation of blood outside of the body of a living subject is described. The pump permits to slow up the speed of the flow of the blood during the circulation outside of the body for the purpose of making determinations of hematochemical parameters of the blood by means of well known apparatuses. The pump comprises a body made of rigid material which is divided in the interior by means of separation plates into three chambers. The first and the last chambers simulate the function of the heart valve while the central chamber simulates the function of a ventricle. A flexible conduit is disposed in the interior of the pump. Blood circulates in the flexible conduit which extends in a rectilinear manner or wound spirally in the interior of the chambers which are completely filled up with incompressible fluid. The peristaltic action of the heart is simulated by means comprising pistons which are staggered and which act in correspondence to each chamber. The action of compression of the piston means corresponds to the compression of the flexible conduit, and therefore, its closure, while the action of depression corresponds to the opening of the flexible conduit. The alternate compression and depression action cause the advance of the flow of blood in the interior of the flexible conduit.

5 Claims, 2 Drawing Figures

HEART PUMP FOR THE CIRCULATION OF BLOOD OUTSIDE THE BODY OF A LIVING SUBJECT

The present invention relates to artificial cardiac pumps and more specifically to artificial cardiac pumps to be used for circulation of the blood outside of the body, which pumps make it possible to slow up the velocity of the flow of the blood during the circulation of the blood outside of the body for the purpose of studying the properties of the blood and determining hematochemical parameters by means of suitable apparatuses capable of making the relevant determinations.

One object of the present invention is to provide a cardiac pump of the type mentioned hereinabove by means of which blood may be removed from the human body, the flow may be slowed up for the purpose of making the biological determinations, for instance by means of non-interfering electrodes and then reintroduced again into circulation in the body without causing serious damages or alterations in the blood.

The achievement of a cardiac pump of this type has been faced with a number of technical difficulties and problems connected with the requirement of maintaining the biological and chemical properties of the blood and the achievement of this sort of pump requires overcoming these difficulties.

First of all, it is necessary to overcome the problem of maintaining the apparatus sterile; it is, therefore, necessary to use a pump which totally avoids biological contamination of the blood for the purpose of not interfering with the well being of the patient and at the same time achieving reliable measurements.

For this purpose, the greater part of the components of the circuit for the circulation of the blood outside of the body usually is intended to be thrown away after a single use; the component parts in other words after having been used with one patient, are substituted for the subsequent patient prior to using the circuit. The parts which are not to be replaced when the apparatus is used with another patient must be made of a material which permits sterilization by common methods such as autoclave, a furnace made of ethylene oxide and sterilizing solutions.

The circuit for the circulation of blood outside of the body and in particular the cardiac pump must avoid the problems resulting from the chemical contamination of blood, that is namely the transfer of ions from the metallic walls or conversely the absorption of ions by the blood from the metallic walls with formation of soluble compounds.

For this purpose, the greater part of the surfaces in contact with blood have been made of a silicon elastomer suitable for medical use while the remaining parts are made with special types of stainless steel which cannot be attacked by organic liquids as well as sterilizing liquids.

The cardiac pump according to the present invention in view of these fundamental requirements for the purpose of achieving the appropriate extracorporeal circulation of the blood and making sure that no damage results to the blood, has provided the first complete solution to the problem of avoiding completely the hemolysis of the blood which is caused by mechanical forces which cause rupture of the blood corpuscles and by too rapid flow which are particularly harmful and which frequently occur during the phase of slowing up and acceleration of the blood flow.

According to one of its fundamental aspects, the cardiac pump according to the present invention permits to eliminate the phenomena of hemolysis because it is provided with means which permit the blood to flow, which means simulate the peristaltic action of human blood and permit the blood to move and at the same time avoid the mechanical action of known apparatuses which cause more or less substantial damage to the blood which is being pumped.

The cardiac pump according to the present invention offers, therefore, an action of transportation and a function which are very similar to those of the real heart: the blood, therefore, is subjected to actions, the properties and parameters of which are substantially the same as in the case of the blood circulation in the human body.

The above object is achieved due to the fact that the cardiac pump according to the present invention reproduces, in accordance with one of its main features in its structure the human heart and simulates the function of the human heart so that the pumping action, which the pump performs is a physiological action and perfectly tolerated by the blood.

The cardiac pump according to the present invention comprises:

a pump body made of rigid material;

a flexible conduit of elastic material in the interior of which the blood flows;

holding means in the interior of the body of the pump capable of dividing the interior volume of the body of the pump into three separate chambers and in each of the chambers there is arranged a portion of the flexible conduit. The chambers are filled completely with an incompressible fluid;

means for rigidifying the tube which are arranged in correspondence to the means for separation of the internal volume of the body of the pump, which means for rigidifying the tube are capable of preventing the collapse of the tube in correspondence to the separation means;

compressing means associated with the pump body in communication with the interior capable of imparting to the fluid contained in the chambers an alternate periodic action of compression and expansion.

The properties and the advantages of the cardiac pump according to the present invention are illustrated in the accompanying drawing together with the following detailed description of one embodiment of the invention, which embodiment, however, is not intended to limit the scope of the invention.

Figure 1:
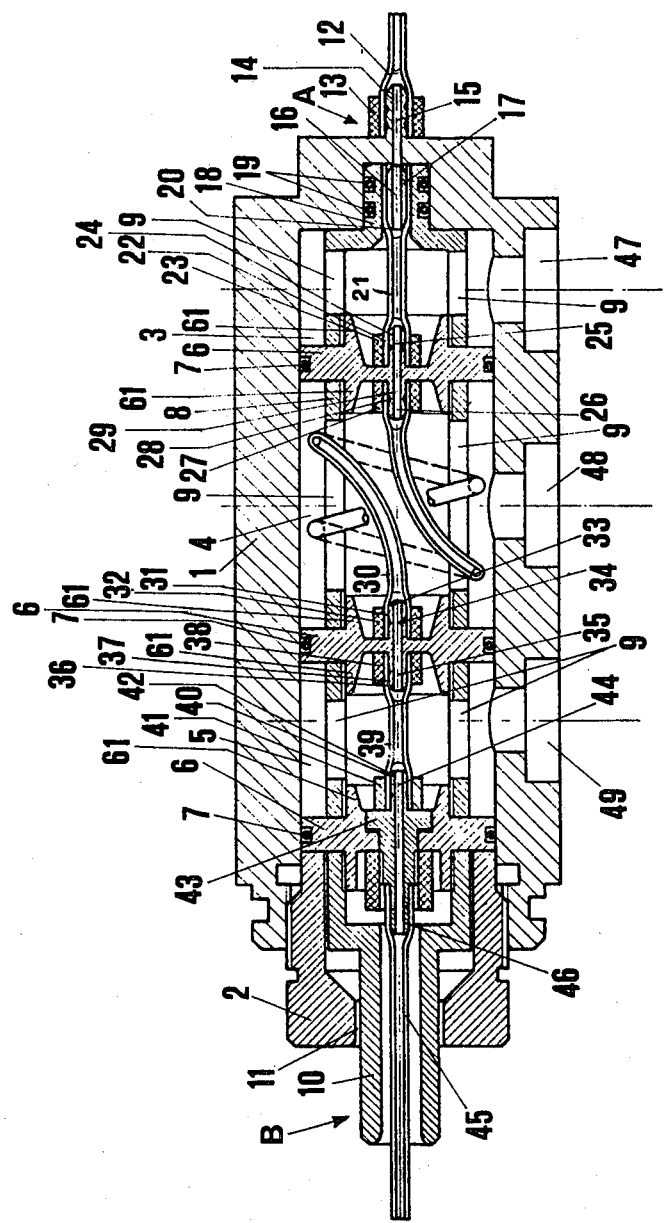
FIG. 1 is a longitudinal cross-section on an enlarged scale of the cardiac pump according to the present invention, showing only the pump body and the interior organs.

With reference to the figures, the pump according to the present invention comprises body 1 made of rigid material, preferably metal, which is closed at one end, that is at the right end. At the opposite end, the apparatus comprises a closure element 2 which is attached to the body by means of a screw for the purpose of permitting the opening of the pump and the eventual substitution of some of the internal elements.

The internal volume of the body of the pump 1 is divided into three chambers 3, 4 and 5 in series by means of separation plates 6. These separation plates 6 consist of, for instance of three discs of diameter equal to the internal diameter of the pump body 1 and they are provided along their contour with means for holding the plates such as, for instance conventional O-Ring 7 which are arranged in the perimetral cavity of the discs 6.

In the interior of the body 1 of the pump there is inserted a cylindrical body designated by the numeral 8, the function of which is to permit the support and the centering of the separation plates or discs 6 as well as the support and centering of the flexible tube as it will be discussed in more detail hereinbelow at the extremity of the inlet and the extremity of the outlet. The cylindrical body 8 is provided with openings 9 which place the space external to the chambers 3, 4 and 5 in communication with the interior of the cylindrical body 8. At the outlet end of the pump, that is on the side where the closure element 2 is attached, the cylindrical body 8 presents a cylindrical part 10 which has a smaller diameter. This cylindrical part 10 goes through an opening 11 of the closure element 2 for the purpose of bringing the flexible conduit to the exterior of the pump.

The chambers 3, 4 and 5 as well as the corresponding internal volumes within the cylindrical body 8 are preliminarily filled with an incompressible liquid such as, for instance apiretyc distilled water so that the total internal volume of the body 1 of the pump is completely filled with liquid.

In the interior of the body 1 of the pump, there is inserted in the manner which will be described hereinbelow a flexible conduit of elastic material through which the blood flows from the inlet end which is represented by the symbol A towards the outlet end which is represented by the symbol B.

The flexible conduit presents the inlet 12 connected to the body 1 of the pump by means of element 13 which is a coupling sleeve fixed onto the external wall of the body 1. In the interior of element 13, is arranged a projection of body 1 of substantially cylindrical shape designated by numeral 14, which projection presents a longitudinal axial opening 15 which communicates with the interior of body 1. The blockage of conduit 12 between the sleeve 13 and the projection 14 results in a seal and for this purpose conventional sealing means are provided which are not shown in detail in the drawing.

Through the longitudinal conduit 15 of the projection 14, the blood in introduced in a longitudinal conduit 16 which is formed in a cylindrical element 17 inserted in a projection 18 of the cylindrical body 8 arranged in the interior of the corresponding cavity of the body 1 of the pump. Conventional sealing means, for instance rings O-Ring 19 are provided between projection 18 and the cavity of the body 1. The cylindrical element 17 and the internal projection 18 permit to achieve blocking means for the extremity 20 of the flexible tube used as an inlet for the blood into the chamber 3, which chamber constitutes the first chamber of the cardiac pump according to the present invention.

The flexible conduit in the interior of the chamber 3 is connected to the opposite end of the preceding chamber in a manner identical to the manner with which the fixing of the conduit to the inlet end is achieved. For this purpose, after the segment of the flexible tube 22 disposed in the interior of the chamber 3, the end 22 is fixed in the interior of a coupling 23 by means of a projection 24 which is formed in a single piece with the separation plate or disc 6. Also, in this case, there are provided sealing means to prevent mixing of the liquid contained in the chamber 3 with the blood which flows in the interior of the flexible tube.

In the interior of the projection 24 of the disc 6 in the longitudinal direction is formed an opening 25 which permits to achieve the flow of blood coming from the segment 21 of the flexible tube from its inlet into the subsequent chamber. The longitudinal opening 25 communicates with a longitudinal opening 26 formed in a portion opposite to the preceding chamber where one notes the coupling 27 corresponding to the coupling 23, the extremity of the flexible tube 28 corresponding to the extremity 22 and the projection 29 corresponding to the projection 24. In the manner, the blood which comes through the segment 21 and which flows through the openings 25 and 26 is introduced into the second chamber of the cardiac pump 4 always in the interior of the flexible conduit.

The flexible conduit in the chamber 4, that is the intermediate chamber, of length greater than the first chamber 3 and the third chamber 5, is wound around the cylindrical body 8, thus forming substantially a pair of spirals, one of which results interrupted in FIG. 1 totally for reasons of improving the clarity. In fact the flexible tube results continuous from the extremity of the inlet A to the extremity of the outlet B.

The extremity of the outlet of the flexible tube in the second chamber 4 is connected to the second separation plate or disc 6, in a manner identical to the manner described hereinabove for the first separation plate or disc 6. In fact also in this case, the segment of the flexible tube 30 which forms the spirals described hereinabove is connected at the end 31 to the interior of the coupling 32 integral with the disc 6. The flexible tube is held by means of the substantially cylindrical projection 33 formed in a single piece with the disc 6. Between the projection and the coupling 32, conventional sealing means, not shown, are provided. In the interior of the projection 33 a longitudinal axial conduit 34 is formed which permits the flow of blood from the flexible tube 30 to the successive chamber 5. The conduit 34 is prolonged by corresponding circuit 35 which is formed in a projection 36, the latter being symmetrical with respect to the projection 33, which, by means of sealing means, which are not shown, permits the blocking of the extremity of the inlet of the flexible tube 37 to the last chamber by means of coupling 38, the latter being symmetrical with respect to the coupling 32.

The flexible tube is extended in a last segment 39 which is disposed within the interior of the last chamber 5, which ends with an extremity 40 blocked between coupling 41 and extension 42 formed in a single piece with closure element 43 of the internal space of cylindrical body 8. The latter is provided with a longitudinal conduit 44 communicating with the terminal portion of the flexible tube 45 connected with the exterior of the pump.

Also, the terminal element 43 is provided with extension 46 on which is fixed the extremity of the outlet of the flexible tube by means of sealing elements which are not shown in the figure.

As it is shown in particular in FIG. 1, the length, that is the extension in the longitudinal direction of the chambers 3, 4 and 5 is different and in particular the length of the chambers 3 and 5 is smaller than the length of the central chamber 4. These dimensions of the first and last chambers 3 and 5 as well as the central chamber 4 has been designed to simulate in a complete fashion the function of the human heart. In fact, the first and last chambers 3 and 5 which have smaller length simulate the functioning of the cardiac valve while the central chamber 4 of greater length simulates the functioning of the ventricle of the heart. Also, the greater length of the flexible tube contained in the interior of the central chamber 4, contributes to simulate the function of the ventricle, this length being substantially greater than the length of the segments disposed in the interior of the first chamber 3 and the last chamber 5.

The chambers 3, 4 and 5 of body 1 of the pump, present radial opening 47, 48 and 49 respectively, which openings place in communication the chambers with means of compression and relaxation, which means will be described hereinbelow and which are capable of simulating the physiological functioning of the human heart.

By reference now in addition to FIG. 1 also FIG. 2, the pump, according to the present invention, presents controlling pistons connected to each of the chambers 3, 4 and 5, which pistons are designated respectively by numerals 50, 51 and 52, which pistons create by means of alternating motion a system of compression or relaxation in the chambers mentioned hereinabove.

The pistons 50, 51 and 52, the cylinders of which 53, 54 and 55 are fixed in any manner to the body 1 of the pump, present their shafts 56, 57 and 58, which are disposed staggered in their motion so as to create alternately and in a staggered fashion the system of compression and relaxation in the chambers 3, 4 and 5.

In particular, the chambers of inlet and outlet 3 and 5 are so predetermined that they are always in opposition, that is when one of these two chambers is in the dispersion stage, the other is in the compression stage and vice versa. In this manner, there is never the possibility of free conduction between the inlet and the outlet of the pump and it is possible to carry out the removal in a manner that can be negative or positive so that the removal of fluid or the reintroduction of fliuid from arterial or venous regions is immaterial.

The cardiac pump may be considered as functioning by means of the following sequence of operations keeping in mind that, by application of a predetermined pressure to any one of the chambers 3, 4 and 5, on simulates the closure of a valve following the collapse or the obstruction of the tubular segment comprised in each of these chambers. On the other hand, when one applies a depression to the chambers 3, 4 and 5, one simulates the opening of a valve by restoring the original shape of the conduction tube of the blood which in this manner may freely flow through the corresponding segment.

By way of example, one may start from chamber 3 under compression so that the segment of the tube which is contained in that chamber is closed and in this manner the flow of blood downstream of this segment is prevented.

When this action of compression is terminated, that is when chamber 3 is subjected to a depression, the segment of the tube reacquires its original shape and the flow of blood starts again within the tube.

In the phase in which a depression is applied to the first chamber 3 after the initial compression, there is maintained in the second chamber 4 constantly an action of compression so that the segment of the tube which is contained in the chamber remains obstructed. Subsequently, an action of depression is exerted with respect to the second chamber 4 and simultaneously a new action of compression in the first chamber 3 so that the blood contained in the interior of the segment of the flexible tube 21 may flow through the incompressible segments mentioned hereinabove into the tubular segment 30, which is contained in the second chamber 4. In this phase, the third chamber 5 is kept under pressure so that the segment of the tube 39 which is contained in the chamber prevents the flow of the blood contained in the second chamber 4. The flow of blood from the second chamber 4 to the third chamber 5 takes place substantially in a manner identical to that described in the first and second chambers 3 and 4. In fact, if one applies an action of compression in the second chamber 4 and a simultaneous action of depression in the third chamber 5, the segment of the tube 30 collapses so much that the blood which is contained in the tube is caused to come out through the imcompressible connection means described hereinabove and the blood in the segment 39 of the third chamber 5 flows from which it is sent through further connection elements described hereinabove to the system of electrodes.

From what has been described hereinabove, it is evident that there is formed a continuous peristaltic sequence through which the pump in accordance with the present invention causes in each chamber a sequence of compression-depression-compression which permits the subsequent flow of the blood in the interior of the segment contained in that chamber and the expulsion towards the subsequent chamber. These periodic actions of compression-depression-compression are applied in a coordinated fashion and in series to the several chambers so that the segments of the tube which are contained in the chambers may be closed and opened for the purpose of controlling the flow of blood in a manner essentially continuous from one chamber to the other. The pump according to the present invention is not used evidently alone, but must be used in combination with another identical pump: in this manner one uses first a pump which causes the blood of the patient to flow to the system of analysis and a second pump which reintroduces the blood into the patient.

The compression gradients, that is the dimensions of the small pistons of control 50, 51 and 52 are regulated in such a fashion as not to entrap or compress the corpuscular elements of the blood in the segments of the tube which simulate the valve.

In this manner, the pump according to the present invention, and therefore, the apparatus which comprises a pair of these pumps differs from the mechanical apparatuses of peristaltic pumping known in the art which have been found to produce an effect of rupture, too high flow and, therefore, damage to the corpuscular elements of the blood.

Several tests carried out on the blood which circulates with the pump according to the present invention and the results of these tests have confirmed experimentally the absence of hemolysis and, therefore, have confirmed the validity of the novel concept of the pump according to the present invention which utilizes a fluid system.

Figure 2:
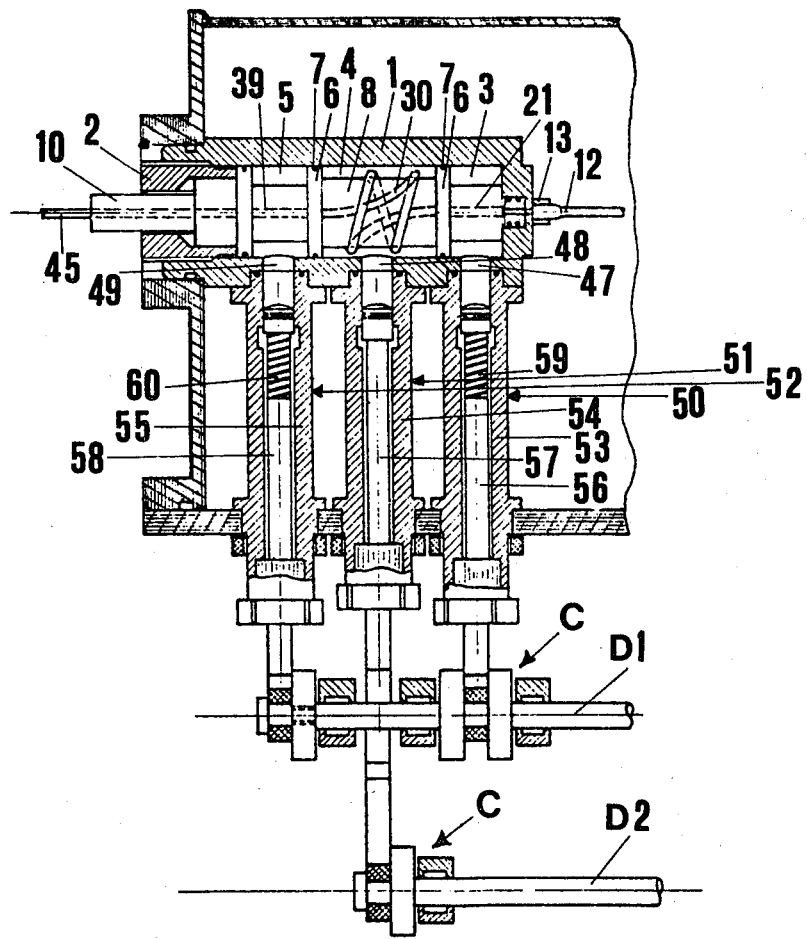
FIG. 2 is a complete view in longitudinal section of the cardiac pump according to the present invention.

The peristaltic action of the pump according to the present invention, that is the cycles of the phases of compression and depression is obtained in the form which is illustrated in FIG. 2 with a system of cams which are not described in detail, which impart to the small pistons the necessary alternating action. These cams which are indicated with the letter C are set in action by two small shafts $D_1$ and $D_2$, which are capable of continuous rotating motion, which motion by means of cams C is transformed in an alternating motion. Obviously, this action with cams could be substituted advantageously by any other element capable of transforming a continuous rotating motion into an alternating motion.

The functioning of the pump according to the present invention results particularly effective because in addition to its original conformation and structure, the dimensioning of the parts is so selected as to permit to achieve a peristaltic action almost identical to that of the human heart. By way of example, there are provided hereinbelow some data of construction of the pump according to the present invention, which, however, have only been provided for the purpose of illustrating the invention and not limiting the invention.

The pump of the present invention functions with a maximum dimension of about 2 meters and the pressures which one can achieve in the chambers 3, 4 and 5 are about one-tenth of one atmosphere. With respect to the flexible tube in the interior of which the blood flows, this tube presents a diameter of about 2 mm. According to one embodiment of the pump according to the present invention, the flexible tube has a diameter of 2.03 mm. The dimensions of the chambers 3, 4 and 5 are selected in a ratio of 1:2 and, therefore, the internal volume of the chambers 3 and 5 is about one-half of that of the central chamber 4. In this chamber, the flexible tube is wound around the body 8 with six turns while in the other two chambers, the tube forms only a rectilinear segment.

The length of the chambers 3, 4 and 5 in the longitudinal direction, that is parallel to the flow of blood, has been particularly contained so that the total space taken by the pump is limited. By way of example, the length of the first and last chambers 3 and 5 has been kept to less tha 20 mm while the length of the central chamber 4, with the ratio stated hereinabove, has been contained to less than 40 mm. Therefore, totally, keeping in mind the space occupied by the valve body 1 and closure element 2, the pump in the embodiment described had a length of about 130 mm.

The advantage of the pump according to the present invention mentioned hereinabove which consists mainly of avoiding the action of rupturing the blood corpuscles and carrying the blood corpuscles away at a high speed, has also been due to the fact that, as it is particularly obvious on the basis of FIG. 2, each one of the pistons 50, 51 and 52 has associated with it a small spring 59 and 60 respectively (the spring of the small central piston 51 is not shown in the figure because it is compressed), which springs make the action of the same pistons more elastic. In this manner, the action exerted by these small pistons on the incompressible fluid present in the chambers 3, 4 and 5 does not occur in a sharp and sudden manner due to mere mechanical forces, but the flow of blood from one segment of the flexible conduit to the subsequent one occurs without damage to the blood itself.

The slowing up of the velocity of the flow of blood in the pump and, therefore, in the apparatus which comprises the two pumps functioning in synchronism, is obtained by gradually adjusting the speed of action of the small pistons 50, 51 and 52. The slowing up which is obtained in the embodiment illustrated is very substantial, such that it permits the determination of hematochemical parameters by a known conventional system of determination. This system of apparatus or apparatuses used for this sort of determinations are well known in the field of study of the blood and are not illustrated nor described in detail here.

The pump according to the present invention is particularly advantageous also if one considers that in the subsequent phases of use, it is possible to substitute the parts of the apparatus which are intended to be used only once with only one patient and also for the necessary operations of maintenance and sterilization. In this connection, by reference to FIG. 1, it is clear that the disassembly of the pump may be performed in a single manner. In fact, it is sufficient to remove the closure element 2 which is threaded and which is screwed on the valve body 1 in order to have access to the interior of the pump. The latter, in fact, may be easily disassembled, first removing by unscrewing the terminal part 10 of the internal body 8. The latter further is made of three segments, each of which is disposed in the interior of the chambers 3, 4 and 5 and each segment is screwed on a longitudinal threaded projection 61 of the elements or separation plates 6.

The several blocking couplings of the flexible tube, that is the couplings 22, 27, 32, 38 and 41 may be applied, for instance by pressure, applied once to the extremity of the flexible tube on the corresponding projections 24, 28, 33, 36 and 42 of the plates 6. In this manner, each element of the pump may be suitably subjected to sterilization so that the pump may be used again for subsequent determinations.

For the purpose of determining the effectiveness of the pump according to the present invention, tests on the manner of functioning have been carried out and specifically examinations of blood which goes through the pump have been made, the results of which are reported hereinbelow. There has been used human blood contained in sterile containers diluted with 3.8% sodium citrate. The blood has been made to recirculate five consecutive times in the machine with a rate of flow of 150 cc/hour simulating a function of about 160 hours in a patient. At start and after each of the five passages, there has been determined:

the number of red corpuscles per ml and the value of the hematocrit with a Coulter Counter;

the plasma concentration of potassium by means of a flame photometer;

plasma concentration of hemoglobin by the modified method of Crosby and Furth (Blood II-380-1956);

the number of plaques by counting under the microscope in phase contrast.

At the beginning and at the end of a single experiment, there are tested:

the osmotic resistance of erythrocytes;

the sterility of the blood by means of cultures of agar-tryptose-thioglycolate;

pH, $PCO_2$ and $PO_2$ are determined with the apparatus IL 213.

In this manner, it has been possible to prove that:

(1) The number of G.R. and the hematocrit if the blood has been suitably mixed prior to the determination varies very little, and in any event, in a statistically irrelevant manner.

(2) The concentration of potassium in the plasma which constitutes an index of hemolysis, has remained almost constant, not only after each single passage, but also if one considers the respective values at the beginning and at the end of the experiments.

(3) The plasma concentration of hemoglobin which has been measured with a particularly sensitive method, has not undergone even minimal variations.

(4) The number of plaques has remained unchanged.

(5) The osmotic resistance of the erythrocytes has not undergone any variations.

(6) The hemocultures have always been maintained sterile.

(7) The pH, $PCO_2$ and $PO_2$, have not undergone variations between the start and the end of each experiment.

From the results discussed hereinabove, it is clear thet the circulation of blood in the apparatus which is the subject of the present invention, not only does not generate hemolysis, but does not create even a reduction in the resistance of the erythrocytes. It is also clear that the blood which is circulated through small tubes used only once or small special steel containers which are easily sterilizable by circulation of sterilizing substances, does not undergo any bacterial contamination and that the parameters determined before and after the circulation of the blood through the apparatus do not undergo modifications, a fact which proves the reliability of the results which may be obtained in accordance with the present invention.

The description of the pump according to the present invention hereinabove obviously has been given by way of illustration and it is possible to make several variations and/or modifications without departing from the scope of the invention.

What is claimed is:

1. A heart pump for the circulation of blood outside of the body of a living subject which comprises:
   (a) a pump body (1) made of rigid material;
   (b) a flexible tube made of elastic material through which the blood flows;
   (c) sealing means (6) disposed in the interior of the body of the pump (1) capable of dividing the internal volume of the body (1) into separate chambers (3,4,5), a segment of the flexible tube going through each of the chambers, said chambers being completely filled of an incompressible fluid;
   (d) means for preventing blockage of the flexible tube arranged in alignment with said sealing means (6) and capable of preventing the collapse of the flexible tube in the location corresponding to said sealing means;
   (e) compression means associated with the valve body (1) and communicating with its interior being capable of imparting to the fluid contained in said chamber an alternating periodic action of compression and expansion, a central body (8) within the interior of the body of the pump made of rigid material; and
   (f) wherein the first and the last chambers (3,5) are of length shorter than the central chamber (4), the length of the flexible tube segment (30) in said central chamber (4) being greater than the length of the flexible tube segments (21,39) respectively, in the first and last chambers (3,5), said segments of the flexible tube (21,39) in the first and the last chambers (3,5) being essentially rectilinear and the segment of the flexible tube (30) in the interior of the central chamber (4) is wound in a spiral fashion around said central body (8).

2. The heart pump according to claim 1, wherein the body (8) in the interior of the valve body (1) is provided with opening (9) capable of permitting the introduction of incompressible liquid in the interior volume of the body (8), said segments of the flexible tube (21,39) of the chambers (3,5) being located in said internal volume of body (8), said portion (30) of the flexible tube in the interior of the chamber (4) also being placed within the internal volume of the body (8).

3. The heart pump according to claim 2, wherein each of said sealing means (6) is provided on both faces thereof with a substantially cylindrical projection made of rigid material, and the pump is provided with external blocking couplings, adapted to block one end of the flexible tube, each of said projections being provided with a longitudinal conduit communicating with the conduit of the projection of the adjacent chamber.

4. The heart pump according to claim 3, wherein the body (8) in the interior of the valve body (1) is made of segments, each of which is immovably attached to the ends of said sealing means (6).

5. The heart pump according to claim 4, wherein each of the chambers (3,4,5) has associated piston means (50,51,52) staggered with respect to one another capable of generating in succession in said chambers by means of the incompressible liquid actions of compression and expansion of the flexible tube in the interior of which the blood flows and wherein said piston means have shafts (56,57,58) respectively, capable of rotating motion, and the pump comprises a system of cams associated with said shafts for the conversion of said rotating motion into an alternating motion and said piston means are provided with elastic means.

* * * * *